(12) United States Patent
Omori et al.

(10) Patent No.: US 10,307,342 B2
(45) Date of Patent: Jun. 4, 2019

(54) ORAL BIOFILM INHIBITOR

(71) Applicant: NATIONAL UNIVERSITY CORPORATION OKAYAMA UNIVERSITY, Okayama-shi, Okayama (JP)

(72) Inventors: Kazuhiro Omori, Okayama (JP); Takashi Ito, Okayama (JP); Shogo Takashiba, Okayama (JP); Masao Irie, Okayama (JP)

(73) Assignee: NATIONAL UNIVERSITY CORPORATION OKAYAMA UNIVERSITY, Okayama-Shi, Okayama (JP)

(*) Notice: Subject to any disclaimer, the term of this patent is extended or adjusted under 35 U.S.C. 154(b) by 0 days.

(21) Appl. No.: 15/505,411

(22) PCT Filed: Aug. 21, 2015

(86) PCT No.: PCT/JP2015/073635
§ 371 (c)(1),
(2) Date: Feb. 21, 2017

(87) PCT Pub. No.: WO2016/027901
PCT Pub. Date: Feb. 25, 2016

(65) Prior Publication Data
US 2017/0273874 A1 Sep. 28, 2017

(51) Int. Cl.
*A61K 6/02* (2006.01)
*A61K 45/00* (2006.01)
(Continued)

(52) U.S. Cl.
CPC ............ *A61K 6/02* (2013.01); *A61K 6/0017* (2013.01); *A61K 6/08* (2013.01); *A61K 8/4926* (2013.01);
(Continued)

(58) Field of Classification Search
CPC ...................................................... A61K 6/02
See application file for complete search history.

(56) References Cited

U.S. PATENT DOCUMENTS 3,431,208 A * 3/1969 Bailey ................... A61K 8/046
424/45
5,330,746 A * 7/1994 Friedman ............... A61K 9/006
424/49

(Continued)

FOREIGN PATENT DOCUMENTS

JP 2002-503520 A 2/2002
JP 2009-167204 A 7/2009

(Continued)

OTHER PUBLICATIONS

International Search Report (PCT/ISA/210) dated Nov. 17, 2015, by the Japanese Patent Office as the International Searching Authority for International Application No. PCT/JP2015/073635.

(Continued)

*Primary Examiner* — San Ming R Hui
(74) *Attorney, Agent, or Firm* — Buchanan, Ingersoll & Rooney PC (57) ABSTRACT

There is provided an oral biofilm inhibitor having an exceptional inhibitory effect on oral biofilm formation. It is an oral biofilm inhibitor comprising a curable composition containing an antimicrobial agent, wherein a compressive strength of a cured product formed by curing the composition is 150 MPa or less, and a content of the antimicrobial agent is 0.001 to 3% by weight. An oral biofilm inhibitor thus obtained is used for inhibiting biofilm formation in an oral cavity by applying a curable composition containing an antimicrobial agent to a dental defect site for allowing the composition to cure at the dental defect site, and then disintegrating the cured composition.

8 Claims, 6 Drawing Sheets (51) Int. Cl.
- *A61K 9/08* (2006.01)
- *A61K 6/08* (2006.01)
- *A61K 8/49* (2006.01)
- *A61Q 11/00* (2006.01)
- *A61K 6/00* (2006.01)

(52) U.S. Cl.
CPC ............... *A61K 9/08* (2013.01); *A61K 45/00* (2013.01); *A61Q 11/00* (2013.01)

(56) References Cited

U.S. PATENT DOCUMENTS

| | | |
|---|---|---|
| 2001/0056133 A1 | 12/2001 | Montgomery et al. |
| 2011/0244431 A1 | 10/2011 | Shinozaki et al. |
| 2012/0027829 A1 | 2/2012 | Hashimoto et al. |
| 2013/0189337 A1 | 7/2013 | Hashimoto et al. |

FOREIGN PATENT DOCUMENTS

| | | |
|---|---|---|
| JP | 2011-213608 A | 10/2011 |
| JP | 2013-43869 A | 3/2013 |
| WO | WO 99/42079 A2 | 8/1999 |
| WO | 02/47572 A1 | 6/2002 |
| WO | 2008/100451 A2 | 8/2008 |

OTHER PUBLICATIONS

Yukinori Kato et al., "Gypsum Temporary Filling Material Containing Tannin-fluoride: On Physical Properties", The Journal of the Japanese Society for Dental Materials and Devices, 1985, vol. 4, No. 4, pp. 307-314.

Tomohiro Asai et al., "Antibacterial Activity of Endodontic Restorative Materials against Oral Bacteria", Nihon Shika Hozongaku Zasshi, 2013, vol. 56, No. 2, pp. 138-143.

Dimkov A et al., "Compressive Strength and Setting Time Determination of Glass-Ionomer Cements Incorporated with Cetylpyridinium Chloride and Benzalkonium Chloride", Contributions Sec. Biol. Med. Sci., 2012, vol. 33, No. 1, pp. 243-263.

Extended Search Report issued by the European Patent Office in corresponding European Patent Application No. 15834162.8-1132 dated Mar. 1, 2018 (6 pages).

Gidwani et al.: "In vitro evaluation of sealing ability and antimicrobial activity of hydraulic temporary sealing materials," Journal of Restorative Dentistry, vol. 2, Issue 1, Jan.-Apr. 2014, pp. 13-19 (7 pages).

Communication pursuant to Article 94(3) EPC issued by the European Patent Office in corresponding European Patent Application No. 15834162.8-1111 dated Jan. 29, 2019 (7 pages).

* cited by examiner

HE stain, x 200

ORAL BIOFILM INHIBITOR

TECHNICAL FIELD

The present invention relates to an oral biofilm inhibitor.

BACKGROUND ART

It has been known that various bacteria and so forth present in an oral cavity cause oral diseases such as dental caries, periodontal disease, gingivitis and halitosis. Generally, in an oral cavity, many of oral bacteria exist not alone, but as a bacterial flora called as a biofilm. In the light of preventing oral diseases, it is, therefore, important to inhibit oral biofilm formation.

Patent Reference No. 1 has described a dental hydraulic temporary sealer composition comprising 10 to 90% by weight of calcium sulfate, 5 to 40% by weight of a vinyl acetate resin, 1 to 40% by weight of an inorganic filler, 1 to 30% by weight of an alcohol with a boiling point of 110° C. or higher and 0.001 to 5% by weight of a nonionic surfactant. The reference has described that there can be provided a dental hydraulic temporary sealer composition which is significantly improved in initial curability, sealability and filling operability in an oral cavity compared to a conventional dental hydraulic temporary sealer. Patent Reference No. 1 has, however, not described or implied inhibition of biofilm formation.

PRIOR ART REFERENCES

Patent References

Patent Reference No. 1: JP 2011-213608 A

SUMMARY OF THE INVENTION

Problems to be Solved by the Invention

To solve the above problems, an objective of the present invention is to provide an oral biofilm inhibitor excellent for inhibiting oral biofilm formation.

Means for Solving the Problems

The above problems can be solved by providing an oral biofilm inhibitor comprising a curable composition containing an antimicrobial agent, wherein a compressive strength of a cured product formed by curing the composition is 150 MPa or less, and a content of the antimicrobial agent is 0.001 to 3% by weight.

Here, preferred is the oral biofilm inhibitor used for inhibiting biofilm formation in an oral cavity by applying a curable composition containing an antimicrobial agent to a dental defect site for allowing the composition to cure at the dental defect site, and then disintegrating the cured composition.

The oral biofilm inhibitor as described above, wherein the curable composition is again applied to the site where the cured composition has been disintegrated, is also a preferable embodiment of the present invention.

The above problems can be also solved by providing an oral biofilm inhibitor kit comprising a curable composition and an antimicrobial agent, wherein a compressive strength of a cured product formed by curing an oral biofilm inhibitor is 150 MPa or less, and the curable composition and the antimicrobial agent are blended for use such that a content of the antimicrobial agent in the oral biofilm inhibitor comes to be 0.001 to 3% by weight.

The above problems can be also solved by providing an oral biofilm inhibitor kit comprising a curable composition and a liquid agent containing water as a main component, wherein at least one of the curable composition and the liquid agent containing water as a main component comprises the antimicrobial agent; a compressive strength of a cured product formed by curing the oral biofilm inhibitor is 150 MPa or less; and the curable composition and the liquid agent are blended for use such that a content of the antimicrobial agent comes to be 0.001 to 3% by weight.

The above problems can be also solved by providing a method for producing an oral biofilm inhibitor comprising a curable composition containing an antimicrobial agent, comprising blending the curable composition and the antimicrobial agent such that a content of the antimicrobial agent in the oral biofilm inhibitor comes to be 0.001 to 3% by weight.

Effects of the Invention

According to the present invention, there can be provided an oral biofilm inhibitor excellent for inhibiting oral biofilm formation.

MODES FOR CARRYING OUT THE INVENTION

The present invention is characterized in an oral biofilm inhibitor comprising a curable composition containing an antimicrobial agent, wherein a compressive strength of a cured product formed by curing the composition is 150 MPa or less, and a content of the antimicrobial agent is 0.001 to 3% by weight. In the present invention, it is extremely important that a compressive strength of a cured product formed by curing the composition is a particular value or less and a content of the antimicrobial agent in the inhibitor is within a particular range. We have found that an oral biofilm inhibitor of the present invention exhibits excellent inhibitory effect to biofilm formation, only when the conditions described above are met.

It is important that a content of the antimicrobial agent in the oral biofilm inhibitor of the present invention is 0.001 to 3% by weight. It has been observed that when a content of the antimicrobial agent is within this range, the inhibitor is antimicrobially effective in a culture medium and a biofilm is not formed on the surface of a cured product. If a content of the antimicrobial agent is more than 3% by weight, inhibiting biofilm formation is difficult. As shown in Examples later, when a cured product with a content of the antimicrobial agent being 5% by weight is immersed in a *S. mutans* culture medium, antimicrobial effect was observed in the culture medium but a biofilm was formed on the surface of the cured product. Surprisingly, it has been found for the first time by our investigation that when a content of the antimicrobial agent in the inhibitor is increased, biofilm inhibitory effect is rather lowered. It is, therefore, significant to employ a formation that a content of the antimicrobial agent is 3% by weight or less.

It is generally known that many of cationic antimicrobial agents are bitter. In the light of suppressing bitterness when it is put into an oral cavity, a lower content of the antimicrobial agent is preferable. Seen from this point of view, a content of the antimicrobial agent is preferably 2% by weight or less, more preferably 1% by weight or less. Furthermore, if a content of the antimicrobial agent is less than 0.001% by weight, biofilm formation cannot be inhibited, and a content of the antimicrobial agent is preferably 0.005% by weight or more, more preferably 0.01% by weight or more.

Herein, there are no particular restrictions to the type of an antimicrobial agent. Examples of an antimicrobial agent include cationic antimicrobial agents such as cetylpyridinium chloride (CPC), thymol and isopropylmethylphenol (IPMP).

In an oral biofilm inhibitor of the present invention, it is also important that a compressive strength of a cured product formed by curing a curable composition containing an antimicrobial agent is 150 MPa or less. If a compressive strength is more than 150 MPa, biofilm formation cannot be inhibited, and a compressive strength is preferably 100 MPa or less, more preferably 50 MPa or less, further preferably 25 MPa or less, particularly preferably 10 MPa or less. If a compressive strength is too low, formability may not be maintained. Therefore, it is generally 0.01 MPa or more, preferably 0.05 MPa or more. A compressive strength of a cured product in the present invention is defined in accordance with "compressive strength test" described in JIS T6602. As seen from Examples later, three cured products are pressed at a crosshead speed of 2 mm/min and a load at the time of crush of the cured products is measured and an average is calculated to determine a compressive strength.

There are no particular restrictions to the type of a curable composition as long as a cured product formed by curing a curable composition containing an antimicrobial agent has a compressive strength of 150 MPa or less. The curable composition is preferably at least one of a hydraulic composition, a photocurable composition and a thermosetting composition. Among these, a hydraulic composition is well handleable because it cures by reaction with a liquid agent containing water as a main component. In this regard, a curable composition is more preferably a hydraulic composition, further preferably, because it cures by reaction with water in saliva, a hydraulic composition containing calcium sulfate as a main component. Herein, a liquid agent containing water as a main component can be pure water or a liquid agent containing water as a main component and other components. Furthermore, a main component refers to a component with a content of generally 50% by weight or more, preferably 80% by weight or more.

There are no particular restrictions to the form of a curable composition before curing, and it is preferably a paste in the light of easy application to an oral cavity.

The oral biofilm inhibitor can contain a component other than an antimicrobial agent as long as the effects of the present invention are not deteriorated; for example, a flavor, a colorant, a thickener can be appropriately added. A content of these components is generally 10% by weight or less, preferably 5% by weight or less.

Herein, preferred is an oral biofilm inhibitor used for inhibiting biofilm formation in an oral cavity by applying a curable composition containing an antimicrobial agent to a dental defect site for allowing the composition to cure at the dental defect site, and then disintegrating the cured composition.

An oral biofilm inhibitor of the present invention has moderate compressive strength, so that the inhibitor may partly disintegrate, for example, by mastication. Thus, owing to disintegration of the inhibitor, the antimicrobial agent contained in the inhibitor is released in an oral cavity. As a result, oral biofilm formation can be more effectively inhibited.

A preferable embodiment of the present invention is applying again a curable composition containing an antimicrobial agent to the site where the cured composition has been disintegrated. Thus, an oral cavity can be consistently kept clean.

There are no particular restrictions to a method of applying a curable composition containing an antimicrobial agent to a dental defect site as long as the dental defect site can be completely sealed. A dental defect site can be a dental defect site due to dental caries or periodontal disease, a dental defect site due to injury, a cavity or the like. There are also no restrictions to a method for curing a curable composition at a dental defect site. When the curable composition is a hydraulic composition containing calcium sulfate as a main component, it reacts with water in saliva and therefore, a curing method is convenient. Water can be, if necessary, applied to the surface of the composition after applying the hydraulic composition to the dental defect site.

Another embodiment of the present invention is an oral biofilm inhibitor kit comprising a curable composition and an antimicrobial agent. Herein, a compressive strength of a cured product formed by curing the oral biofilm inhibitor is 150 MPa or less. The kit is provided for use by blending the components such that a content of the antimicrobial agent in the oral biofilm inhibitor comes to be 0.001 to 3% by weight.

Another embodiment of the present invention is an oral biofilm inhibitor kit comprising a curable composition and a liquid agent containing water as a main component. Here, at least one of the curable composition and the liquid agent containing water as a main component contains an antimicrobial agent. A compressive strength of a cured product formed by curing an oral biofilm inhibitor is 150 MPa or less. The kit is provided for use by blending the components such that a content of an antimicrobial agent in the oral biofilm inhibitor comes to be 0.001 to 3% by weight.

There are no particular restrictions to a method for producing an oral biofilm inhibitor of the present invention; specifically, a curable composition and an antimicrobial agent are blended such that a content of the antimicrobial agent in the oral biofilm inhibitor comes to be 0.001 to 3% by weight. The curable composition and the antimicrobial agent can be blended by, but not limited to, manual mixing, a mixing device or the like. The curable composition and the antimicrobial agent can be blended for preparing the inhibitor immediately before application to a dental defect site. Herein, when a liquid agent containing water as a main component is used, a liquid agent containing water as a main component can be blended with a curable composition containing an antimicrobial agent, or a liquid agent containing water as a main component and antimicrobial agent can be blended with a curable composition.

Since an oral biofilm inhibitor of the present invention is excellent in inhibitory effects on oral biofilm formation, it could be used to various applications. Supposed subjects are, in addition to patients with an oral disease, immune-compromised patients (for example, patients with cancer under therapy), elderly adults and the like. When a patient is immune-compromised, risk of developing various systemic diseases is increased. Such a systemic disease that can be mentioned is, for example, aspiration pneumonia. Aspiration pneumonia refers to a disease where oral bacteria invade a lung through misswallowing and grow in the lung, causing inflammation. Invasion by oral bacteria into a lung does not necessarily lead to development of pneumonia, but when immunity is compromised, risk of developing aspiration pneumonia is increased. By applying an oral biofilm inhibitor of the present invention to an oral cavity, various systemic diseases such as aspiration pneumonia can be prevented.

Since an oral biofilm inhibitor of the present invention can be conveniently used, it can be used not only in a dental clinic but also in home care. Furthermore, it can be used in a wide-scale disaster site. If a wide-scale disaster occurs, it becomes difficult to keep an oral cavity clean due to disrupted water supply, leading to deteriorated hygienic environment in the oral cavity. Thus, it may cause a systemic disease as described above. Since an oral cavity can be consistently kept clean by use an oral biofilm inhibitor of the present invention, the use of the inhibitor in a wide-scale disaster site offers particularly numerous benefits.

EXAMPLES

The present invention will be further specifically described with reference to Examples.

Example 1

Production of a cured product

A cured product was produced as described below.

(1) 1.99 g of dental hydraulic temporary sealer ("Caviton", from GC Corporation) and 0.01 g of cetylpyridinium chloride (hereinafter, sometimes abbreviated as "CPC") were blended at room temperature to give a mixture.

(2) a mold with a diameter of 5 mm and a depth of 10 mm was filled with the mixture obtained.

(3) this mold was immersed in distilled water.

(4) after immersion of the mold in distilled water for 24 hours, the mold was removed from the distilled water.

(5) the removed mold was placed in a drying chamber (37° C.).

(6) after placing the mold in the drying chamber for 3 days, the mold was removed from the drying chamber and the cylindrical cured product was taken out from the mold.

Measurement of Strength

Figure 1:
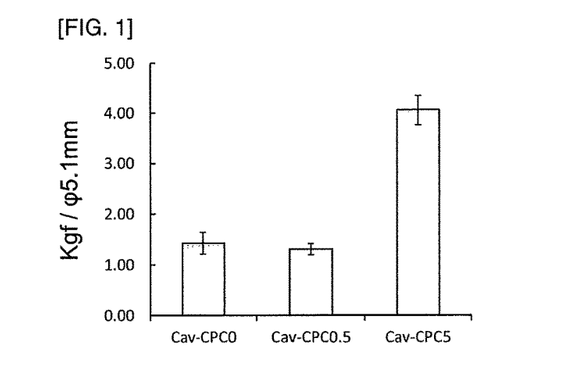
FIG. 1 is a graph showing compressive strength of a cured product in Example 1, and Comparative Examples 1 and 2.

A compressive strength of the cured product obtained was measured in accordance with "compressive strength test" described in JIS T6602. The measurement was conducted for three cured products; the cured product was pressed at a crosshead speed of 2 mm/min and a load at the time of crush of the cured product was measured and an average was calculated. The cured product used for the measurement had an average diameter of 5.1 mm and an average height of 10.6 mm. A measurement apparatus used was "Autograph AG-X 20 kN" from Shimadzu Corporation. As a result, a compressive strength per 5.1 mm diameter of the cured product was 1.31 kgf/φ5.1 mm. It was converted to a compressive strength per unit area (MPa), which was 0.63 MPa. The results are shown in Table 1 and FIG. 1.

Evaluation of Irritation to Oral Mucous Membrane

For evaluating irritation to oral mucous membrane of a cured product extract, a buccal-pouch mucous membrane irritation examination using a Syrian hamster was conducted. A cured product extract was obtained by extracting the cured product with 200 mL of PBS per 1 g of the product at 37° C. for 12 hours. The cured product extract was applied 4 times every 1 hour to the inside of the right buccal pouch of each of five Syrian hamsters. The buccal pouch mucous membrane was visually observed for up to 24 hours after the final application and at the end of visual observation, the animal was euthanized by overdose of pentobarbital. Then, both right and left buccal pouches were isolated and subjected to histopathological examination. The left buccal pouch was used as an untreated control.

Figure 2:
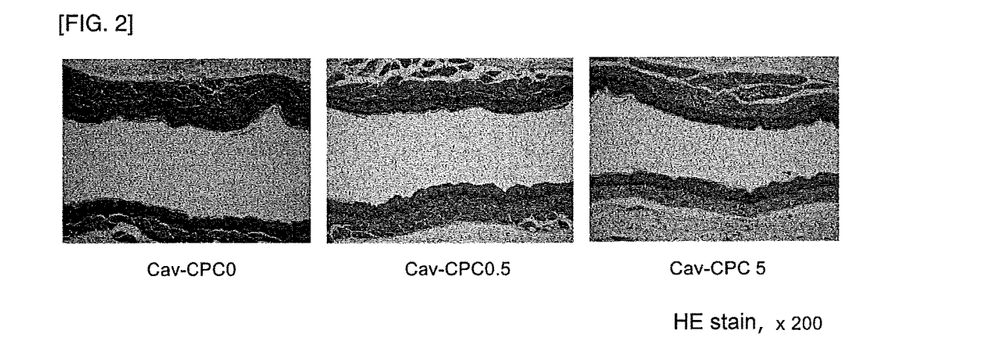
FIG. 2 is a photograph of histopathological examination in Example 1, and Comparative Examples 1 and 2.

Examination name: buccal pouch mucous membrane irritation examination of a CPC-containing Caviton extract using hamsters Examination number: G102 (590-005), GLP: not applicable Examiner: Public Interest Incorporated Foundation, Bio-Safety Research Center As a result, the cured product extract was judged to be nonirritating to the buccal pouch mucous membrane of the syrian hamster. FIG. 2 (Cav-CPC0.5) is a photograph of the histopathological examination.

Evaluation of Antimicrobial Effect

Preparation of an *S. mutans* Culture Medium

An *S. mutans* culture medium was prepared as described below.

(1) *Streptococcus mutans* ATCC25175 strain was cultured under aerobic conditions at 37° C., using Bacto™ Brain Heart Infusion (Becton, Dickinson and Company, Sparks, Md., USA) liquid culture medium.

(2) After cultivation to a logarithmic growth phase under aerobic conditions, an absorbance at a wavelength of 660 nm (A660) was measured using an absorption spectrometer ("SPECTRONIC 20A", from Shimadzu Corporation), and the cultivated medium was diluted to $1 \times 10^5$ cfu/mL with the above liquid medium, to prepare a bacterial suspension.

Figure 3:
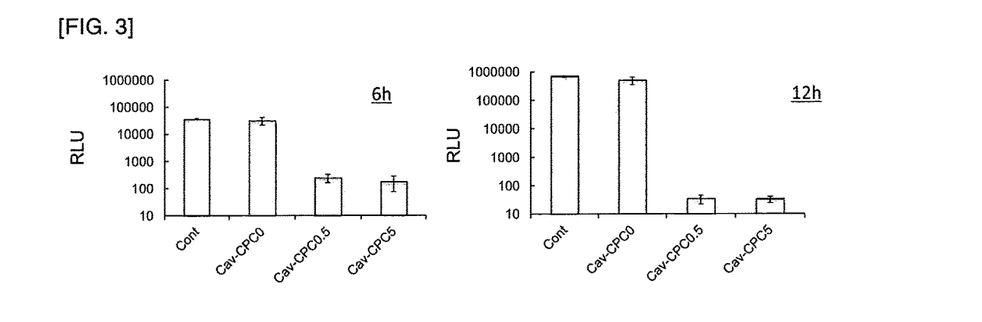
FIG. 3 is a graph showing the amount of ATP in a culture medium after 6 and 12 hours in Example 1, and Comparative Examples 1 and 2.

Evaluation of Bacterial Proliferation Activity 12 milliliter of the culture medium prepared was taken and kept at 37° C., and the cured product was immersed in the culture medium. 48 hours after immersion of the cured product in the culture medium, the cured product was taken off from the culture medium. Here, for measuring the amount of ATP in the culture medium, the culture medium was taken 6 and 12 hours after immersion of the cured product in the culture medium. Then, the amount of ATP in the culture medium was measured using a testing kit and a tester ("Lucifer HS set" and "Lumitester C-110" from Kikkoman Biochemifa Company). The amount of ATP in the culture medium at 6 and 12 hours is shown in Table 1 and FIG. 3. Table 1 and FIG. 3 show that the smaller RLU (luminescence amount) is, the more bacterial proliferation is suppressed. In FIG. 3, "Cont" indicates RLU of the culture medium after 6 hours (average: 37206.0, standard deviation: 1857.2) and after 12 hours (average: 689864.7, standard deviation: 38395.5) when the cured product was not immersed in the culture medium.

Evaluation of Biofilm Inhibition

Microscopic Observation

Figure 4:
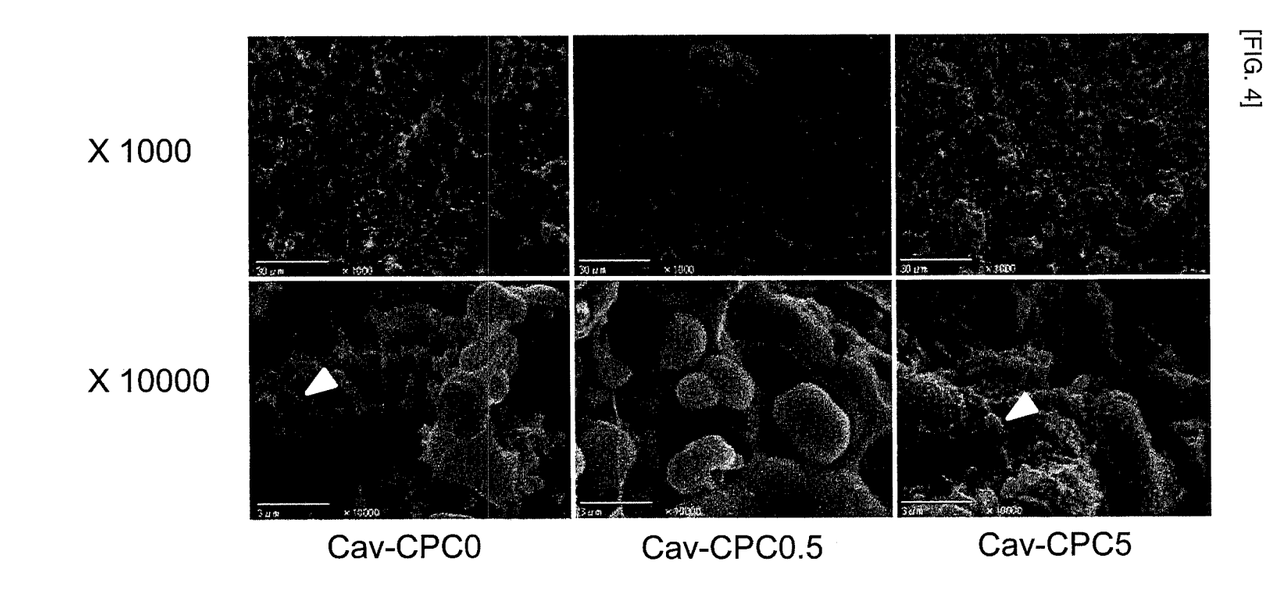
FIG. 4 is an electron microgram of the surface of a cured product after immersion in a culture medium in Example 1, and Comparative Examples 1 and 2 (magnification: 1000 and 10000).

The surface of the cured product removed from the culture medium was observed by a field emission-type scanning electron microscope. FIG. 4 shows an electron micrograph at a magnification of 1000 and an electron micrograph at a magnification of 10000. For the electron micrograms ("Cav-CPC0.5", "×10000"), the presence of bacteria on the surface of the cured product was visually observed. As a result, no bacteria were observed and biofilm was not formed on the cured product. The field emission-type scanning electron microscope used was "FE-SEM DS-720" from Topcon Corporation.

Example 2

Figure 8:
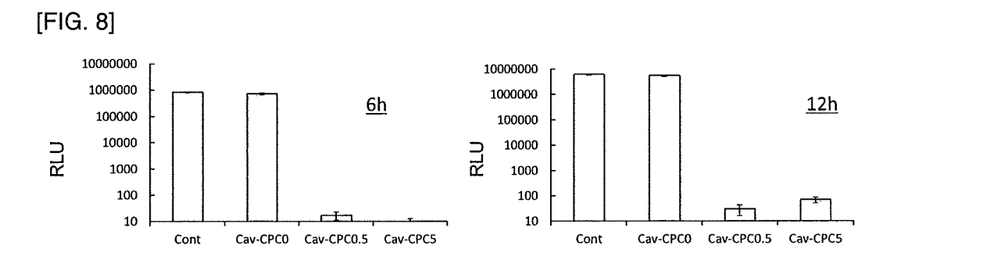
FIG. 8 is a graph showing the amount of ATP in a culture medium after 6 and 12 hours in Example 2, and Comparative Examples 6 and 7.
Figure 9:
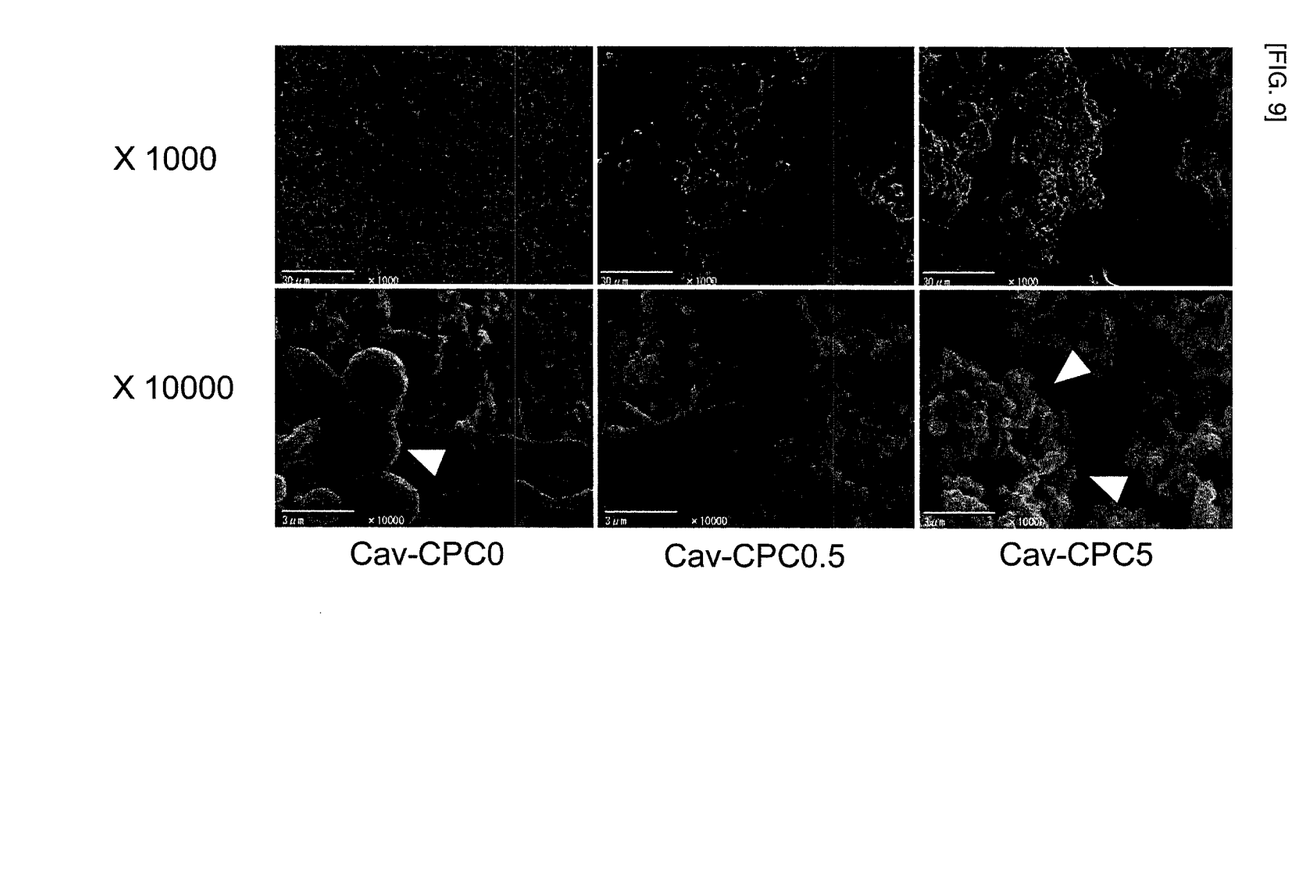
FIG. 9 is an electron microgram of the surface of a cured product after immersion in a culture medium in Example 2, and Comparative Examples 6 and 7 (magnification: 1000 and 10000).

"Evaluation of bacterial proliferation activity" and "Evaluation of biofilm inhibition" were conducted as described in Example 1, using a *Candida albicans* culture medium prepared as described below. The amount of ATP in the culture medium at 6 and 12 hours is shown in Table 2 and FIG. 8. FIG. 9 shows an electron micrograph at a magnification of 1000 and an electron micrograph at a magnification of 10000 (Cav-CPC0.5). As a result, no bacteria were observed and biofilm was not formed on the cured product.

(1) *C. albicans* (clinical isolate) was cultured under aerobic conditions at 37° C., using Bacto™ Brain Heart Infusion (Becton, Dickinson and Company, Sparks, Md., USA) liquid culture medium.

(2) After cultivation to a logarithmic growth phase under aerobic conditions, an absorbance at a wavelength of 660 nm (A660) was measured using an absorption spectrometer ("miniphoto 518R", from TAITEC Corporation), and the cultivated medium was diluted to $1 \times 10^5$ cfu/mL with the above liquid medium, to prepare a bacterial suspension.

Comparative Example 1

A cured product was produced as described in Example 1, except that 1.90 g of Caviton and 0.1 g of CPC were blended at room temperature to afford a mixture in "Production of a cured product" in Example 1. Then, "Measurement of strength", "Evaluation of antimicrobial effect" and "Evaluation of biofilm inhibition" were conducted as described in Example 1. The results obtained are shown in Table 1 and FIGS. 1, 3 and 4. As shown in FIG. 4, the presence of bacteria on the surface of the cured product was visually observed for the electron micrograph obtained ("Cav-CPC5", "×10000"). As a result, in the area of the electron micrograph (13 μm×9 μm), 45 bacteria (arrow in the photograph) were observed, indicating biofilm formation on the cured product. Furthermore, "Evaluation of irritation to oral mucous membrane" was conducted as described in Example 1. As a result, the cured product extract was judged to be nonirritating to the buccal pouch mucous membrane of the syrian hamster. FIG. 2 (Cav-CPC5) is a photograph of the histopathological examination.

Comparative Example 2

A cured product was produced as described in Example 1, except that CPC was absent and 2 g of Caviton was used in "Production of a cured product" in Example 1. Furthermore, "Measurement of strength", "Evaluation of antimicrobial effect" and "Evaluation of biofilm inhibition" were conducted as described in Example 1. The results obtained are shown in Table 1 and FIGS. 1, 3 and 4. As shown in FIG. 4, the presence of bacteria on the surface of the cured product was visually observed for the electron micrograph obtained ("Cav-CPC0", "×10000"). As a result, in the area of the electron micrograph (13 μm×9 μm), 208 bacteria (arrow in the photograph) were observed, indicating biofilm formation on the cured product. Furthermore, "Evaluation of irritation to oral mucous membrane" was conducted as described in Example 1. As a result, the cured product extract was judged to be nonirritating to the buccal pouch mucous membrane of the Syrian hamster. FIG. 2 (Cav-CPC0) is a photograph of the histopathological examination.

Comparative Example 3

Figure 5:
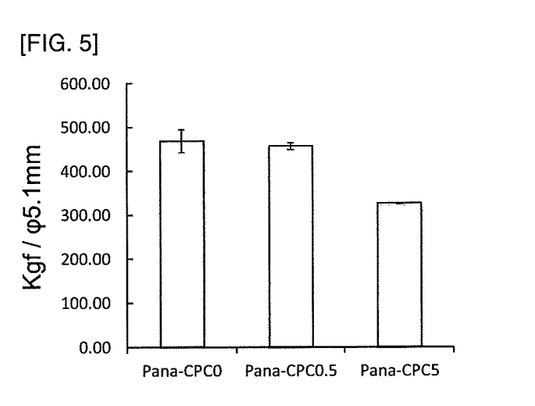
FIG. 5 is a graph showing compressive strength of a cured product in Comparative Examples 3 to 5.
Figure 6:
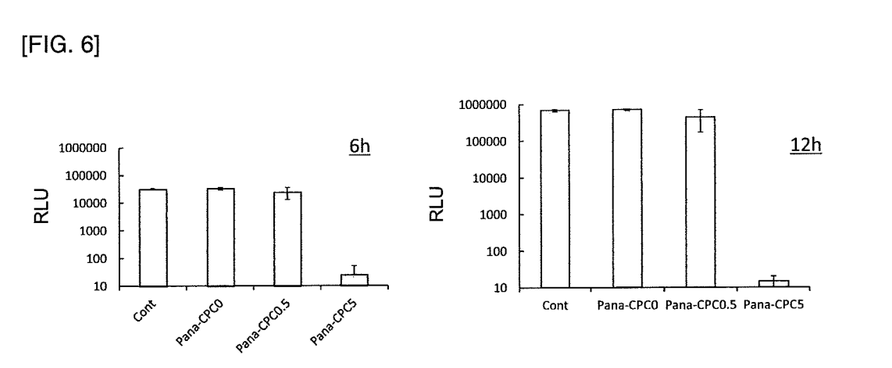
FIG. 6 is a graph showing the amount of ATP in a culture medium after 6 and 12 hours in Comparative Examples 3 to 5.
Figure 7:
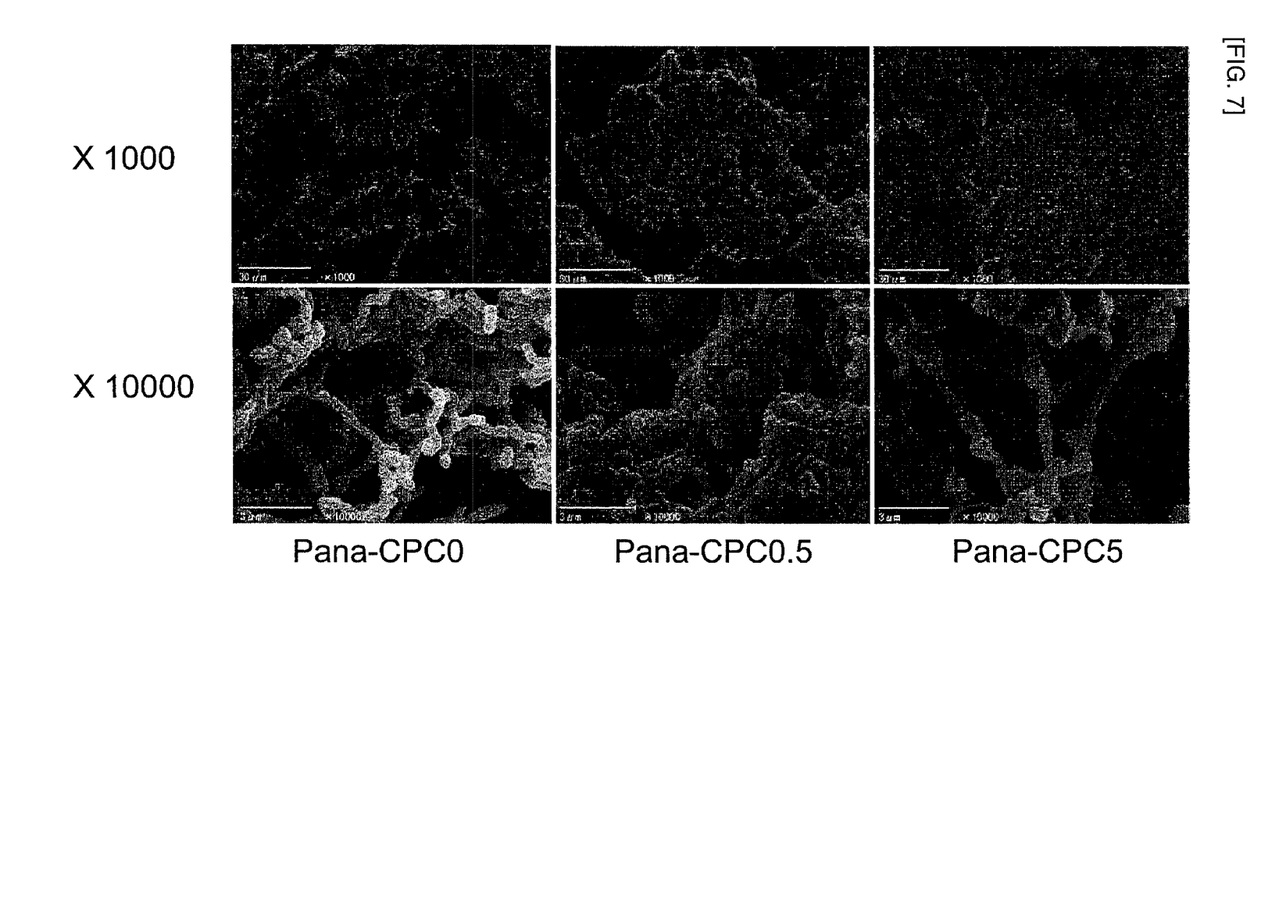
FIG. 7 is an electron microgram of the surface of a cured product after immersion in a culture medium in Comparative Examples 3 to 5 (magnification: 1000 and 10000).

A cured product was produced as described in Example 1, except that in "Production of a cured product" in Example 1, a dental hydraulic temporary sealer was changed to "Panavia F" from Morita Corporation and 0.4975 g of Panavia F and 0.0025 g of CPC were blended at room temperature to afford a mixture. Then, "Measurement of strength", "Evaluation of antimicrobial effect" and "Evaluation of biofilm inhibition" were conducted as described in Example 1. The results obtained are shown in Table 1 and FIGS. 5 to 7. In Comparative Examples 3 to 5, an *S. mutans* culture medium was newly prepared as described in Example 1. In FIG. 6, "Cont" indicates RLU of the culture medium after 6 hours (average: 33152, standard deviation: 433) and after 12 hours (average: 682856, standard deviation: 44861) when the cured product was not immersed in the culture medium. As shown in FIG. 7, the presence of bacteria on the surface of the cured product was visually observed for the electron micrograph obtained ("Pana-CPC0.5", "×10000"). As a result, in the area of the electron micrograph (13 μm×9 μm), more than 300 bacteria were observed, indicating biofilm formation on the cured product.

Comparative Example 4

A cured product was produced as described in Example 1, except that in "Production of a cured product" in Example 1, a dental hydraulic temporary sealer was changed to "Panavia F" from Morita Corporation and 0.475 g of Panavia F and 0.025 g of CPC were blended at room temperature to afford a mixture. Then, "Measurement of strength", "Evaluation of antimicrobial effect" and "Evaluation of biofilm inhibition" were conducted as described in Example 1. The results obtained are shown in Table 1 and FIGS. 5 to 7. As shown in FIG. 7, the presence of bacteria on the surface of the cured product was visually observed for the electron microgram obtained ("Pana-CPC5", "×10000"). As a result, in the area of the electron microgram (13 μm×9 μm), 60 bacteria were observed, indicating biofilm formation on the cured product.

Comparative Example 5

A cured product was produced as described in Example 1, except that in "Production of a cured product" in Example 1, a dental hydraulic temporary sealer was changed to "Panavia F" from Morita Corporation and CPC was absent and 0.5 g of Panavia F was used. Then, "Measurement of strength", "Evaluation of antimicrobial effect" and "Evaluation of biofilm inhibition" were conducted as described in Example 1. The results obtained are shown in Table 1 and FIGS. 5 to 7. As shown in FIG. 7, the presence of bacteria on the surface of the cured product was visually observed for the electron microgram obtained ("Pana-CPC0", "×10000"). As a result, in the area of the electron microgram (13 μm×9 μm), more than 300 bacteria were observed, indicating biofilm formation on the cured product.

Comparative Example 6

A cured product was produced as described in Example 1, except that in "Production of a cured product" in Example 1, 1.90 g of Caviton and 0.1 g of CPC were blended at room temperature to afford a mixture. Then, "Evaluation of bacterial proliferation activity" and "Evaluation of biofilm inhibition" were conducted as described in Example 1, using the *Candida albicans* culture medium prepared in Example 2. The amount of ATP in the culture medium at 6 and 12 hours is shown in Table 2 and FIG. 8. FIG. 9 shows an electron microgram at a magnification of 1000 and an electron microgram at a magnification of 10000 (Cav-CPC5). As a result, in the area of the electron microgram (13 μm×9 μm), more than 300 bacteria (the arrow in the photograph) were observed, indicating biofilm formation on the cured product.

Comparative Example 7

A cured product was produced as described in Example 1, except that in "Production of a cured product" in Example 1, CPC was absent and 2 g of Caviton was used. Then, "Evaluation of bacterial proliferation activity" and "Evaluation of biofilm inhibition" were conducted as described in Example 1, using the *Candida albicans* culture medium prepared in Example 2. The amount of ATP in the culture medium at 6 and 12 hours is shown in Table 2 and FIG. 8. FIG. 9 shows an electron microgram at a magnification of 1000 and an electron microgram at a magnification of 10000 (Cav-CPC0). As a result, in the area of the electron microgram (13 μm×9 μm), more than 300 bacteria (the arrow in the photograph) were observed, indicating biofilm formation on the cured product.

TABLE 1

| | Cured product | | | | | | Compression strength (kgf/φ5 mm, MPa) | | | | |
| | Curable composition (brand) | Antimicrobial agent (% by weight) | Notation | RLU after 6 hours | | RLU after 12 hours | | Average | | Standard deviation | | No. of bacteria |
| | | | | Average | Standard deviation | Average | Standard deviation | kgf/φ5 mm | MPa | kgf/φ5 mm | MPa | |
|---|---|---|---|---|---|---|---|---|---|---|---|---|
| Example 1 | Caviton | 0.5 | Cav-CPC0.5 | 251.0 | 84.9 | 33.7 | 11.6 | 1.31 | 0.63 | 0.11 | 0.05 | 0 |
| Comparative Example 1 | Caviton | 5 | Cav-CPC5 | 183.7 | 108.2 | 32.7 | 8.4 | 4.06 | 1.95 | 0.30 | 0.14 | 45 |
| Comparative Example 2 | Caviton | 0 | Cav-CPC0 | 31772.7 | 10064.1 | 501523.0 | 142926.7 | 1.43 | 0.69 | 0.22 | 0.10 | 208 |
| Comparative Example 3 | Panavia F | 0.5 | Pana-CPC0.5 | 24763 | 11415 | 438532 | 263885 | 456.29 | 223.30 | 7.78 | 6.40 | more than 300 |
| Comparative Example 4 | Panavia F | 5 | Pana-CPC5 | 25 | 27 | 15 | 5 | 326.57 | 160.86 | 1.35 | 2.41 | 60 |
| Comparative Example 5 | Panavia F | 0 | Pana-CPC0 | 33485 | 3925 | 716111 | 35169 | 468.76 | 227.11 | 25.96 | 23.92 | More than 300 |

TABLE 2

| | Cured product | | | RLU | | | | |
| | Curable composition (brand) | Antimicrobial agent (% by weight) | Notation | after 6 hours | | after 12 hours | | No. of bacteria |
| | | | | Average | Standard deviation | Average | Standard deviation | |
|---|---|---|---|---|---|---|---|---|
| Example 2 | Caviton | 0.5 | Cav-CPC0.5 | 17 | 6 | 30 | 14 | 0 |
| Comparative Example 6 | Caviton | 5 | Cav-CPC5 | 10 | 3 | 70 | 18 | more than 300 |
| Comparative Example 7 | Caviton | 0 | Cav-CPC0 | 745142 | 56511 | 5489307 | 235605 | more than 300 |

The invention claimed is:

1. An oral biofilm inhibitor consisting of a curable composition containing cetylpyridinium chloride in paste form and which is at least one of a hydraulic composition, a photocurable composition or a thermosetting composition, wherein a compressive strength of a cured product formed by curing the composition is 10 MPa or less, and a content of the cetylpyridinium chloride is 0.001 to 3% by weight.

2. The oral biofilm inhibitor according to claim 1, used for inhibiting biofilm formation in an oral cavity by applying the curable composition containing the cetylpyridinium chloride to a dental defect site for allowing the composition to cure at the dental defect site, and then disintegrating the cured composition.

3. The oral biofilm inhibitor according to claim 2, wherein the curable composition is again applied to the site where the cured composition has been disintegrated.

4. An oral biofilm inhibitor kit comprising a curable composition and cetylpyridinium chloride in paste form and which is at least one of a hydraulic composition, a photocurable composition or a thermosetting composition, wherein
a compressive strength of a cured product formed by curing an oral biofilm inhibitor is 10 MPa or less, and
the curable composition and the cetylpyridinium chloride are blended for use such that a content of the cetylpyridinium chloride in the oral biofilm inhibitor comes to be 0.001 to 3% by weight.

5. An oral biofilm inhibitor kit comprising a curable composition in paste form which is at least one of a hydraulic composition, a photocurable composition or a thermosetting composition and a liquid agent containing water as a main component, wherein
at least one of the curable composition and the liquid agent containing water as a main component comprises the cetylpyridinium chloride,
a compressive strength of a cured product formed by curing the oral biofilm inhibitor is 10 MPa or less, and
the curable composition and the liquid agent are blended for use such that a content of the cetylpyridinium chloride comes to be 0.001 to 3% by weight.

6. A method for producing an oral biofilm inhibitor comprising a curable composition containing cetylpyridinium chloride according to claim 1, comprising blending the curable composition and the cetylpyridinium chloride such that a content of the cetylpyridinium chloride in the oral biofilm inhibitor comes to be 0.001 to 3% by weight.

7. A method for producing an oral biofilm inhibitor comprising a curable composition containing cetylpyridinium chloride according to claim 2, comprising blending the curable composition and the cetylpyridinium chloride such that a content of the cetylpyridinium chloride in the oral biofilm inhibitor comes to be 0.001 to 3% by weight.

8. A method for producing an oral biofilm inhibitor comprising a curable composition containing cetylpyridinium chloride according to claim 3, comprising blending the curable composition and the cetylpyridinium chloride such that a content of the cetylpyridinium chloride in the oral biofilm inhibitor comes to be 0.001 to 3% by weight.

* * * * *